United States Patent
De Simone

(10) Patent No.: US 7,223,591 B2
(45) Date of Patent: May 29, 2007

(54) STRAIN OF LACTIC ACID BACTERIUM AND EDIBLE COMPOSITIONS, DRUGS AND VETERINARY PRODUCTS CONTAINING IT

(75) Inventor: Claudio De Simone, Ardea (IT)

(73) Assignee: VSL Pharmaceuticals, Inc., Gaithersburg, MD (US)

( * ) Notice: Subject to any disclaimer, the term of this patent is extended or adjusted under 35 U.S.C. 154(b) by 273 days.

(21) Appl. No.: 10/491,885

(22) PCT Filed: Dec. 19, 2002

(86) PCT No.: PCT/IT02/00812

§ 371 (c)(1), (2), (4) Date: Apr. 7, 2004

(87) PCT Pub. No.: WO03/055984

PCT Pub. Date: Jul. 10, 2003

(65) Prior Publication Data

US 2004/0248278 A1    Dec. 9, 2004

(30) Foreign Application Priority Data

Dec. 21, 2001   (IT) .................. RM2001A0763

(51) Int. Cl.
C12N 1/20 (2006.01)
A01N 63/00 (2006.01)

(52) U.S. Cl. .............. 435/253.4; 435/252.1; 435/885; 424/93.44; 424/93.4

(58) Field of Classification Search ............ 435/252.1, 435/253.4, 885; 424/93.4, 93.44
See application file for complete search history.

(56) References Cited

U.S. PATENT DOCUMENTS 5,716,615 A * 2/1998 Cavaliere Vesely et al. ..... 424/93.4
5,760,010 A   6/1998 Klein
6,225,104 B1 * 5/2001 Cavaliere Vesely et al. ..... 435/252.1
6,297,229 B1  10/2001 Lindor

FOREIGN PATENT DOCUMENTS

WO    99 29330 A      6/1999
WO    WO 99/42568 *   8/1999

OTHER PUBLICATIONS

Marshall et al, "Fermentation of milk by Streptococcus salivarius subspecies Salivarius and Streptococcus salivarius subspecies Thermophilus and their use to the yoghurt manufacturer", Journal of Applied Bacteriology, 1985, 59, 147-151; XP009009568.
Sheth Sunil G et al: "Nonalcoholic steatohepatitis." Annals of Internal Medicine, vol. 126, No. 2, 1997, pp. 137-145, XP009006803 ISSN:0003-4819 cited in the application.
O'Conner B J et al: "Nonalcoholic fatty liver (NASH syndrome)." The Gastroenterologist. United States Dec. 1997, vol. 5, No. 4, Dec. 1997, pp. 316-329, XP009009572 ISSN: 1065-2477.
Oneta Carl M et al: "Non-alcoholic fatty liver disease: Treatment options based on pathogenic considerations." Swiss Medical Weekly, vol. 132, No. 35-36, Sep. 7, 2002, pp. 493-505, XP009009570 ISSN: 1424-7860.
Hookman Perry et al: "Current biochemical studies of non-alcoholic fatty liver disease (NAFLD) and non-alcoholic steatohepatitis (NASH) suggest a new therapeutic approach." The American Journal of Gastroenterology. United States Feb. 2003, vol. 98, No. 2, Feb. 2003, pp. 495-499, XP009009569 ISSN: 0002-9270.
Maher J: "The CYP2E1 knockout delivers another punch: first ASH, now NASH. Alcoholic steatohepatitis. Nonalcoholic steatopepatitis." Hepatology (Baltimore, MD) United States Jan. 2001, vol. 33, No. 1, Jan. 2001, pp. 311-312, XP009009574 ISSN: 0270-9139.
Sahai Atul et al: "Upregulation of an Inflammatory Cytokine Osteopntin Precedes Steatohepatitis in a Mouse Model of NASH." Hepatology, vol. 36, No. 4 Part 2, Oct. 2002, p. 405 A XP009009575 53RD Annual Meeting on the Liver; Boston, MA, USA; Nov. 1-5, 2002, http://hepatology.assldjournals.org/scripts/om.dll/serve?action=searchdb&searchdbfor=home&id=jhep Oct. 2002 ISSN: 0270-9139.

* cited by examiner

Primary Examiner—Vera Afremova
(74) Attorney, Agent, or Firm—Nixon & Vanderhye P.C.

(57) ABSTRACT

Describes a new strain of Streptococcus thermophilus ssp. salivarius (deposited on 4 Dec. 2001 at the DSMZ—Deutsche Sammlung von Mikroorganismen und Zellkulturen GmbH, Braunschweig, Germany, with accession No. DSM 14667) and edible compositions, drugs and veterinary products containing it. The use of the said strain is particularly effective in the prevention/treatment of hepatic steatosis (fatty liver) and in nonalcoholic hepatic steatosis.

4 Claims, No Drawings

STRAIN OF LACTIC ACID BACTERIUM AND EDIBLE COMPOSITIONS, DRUGS AND VETERINARY PRODUCTS CONTAINING IT

This application is the US national phase of international application PCT/IT02/00812, filed in English on 19 Dec. 2002, which designated the US. PCT/IT02/00812 claims priority to IT Application No. RM2001A00763 filed 21 Dec. 2001. The entire contents of these applications are incorporated herein by reference.

The present invention relates to a new, biologically pure strain of *Streptococcus thermophilus* ssp. *salivarius* (CD8) deposited on 4 Dec. 2001 at the DSMZ—Deutsche Sammlung von Mikroorganismen und Zellkulturen GmbH, Braunschweig, Germany, with accession No. DSM 14667 and its descendants and mutants.

The present invention further relates to edible compositions, drugs and veterinary products containing the said new strain CD8 as active principle (or as one of the active principles) and the use of the aforesaid strain for preparing edible compositions, drugs and veterinary products for the prevention/treatment of various warning and predictive signs of potentially pathologic conditions or of manifestly obvious pathologies.

With regard to the use of the edible compositions and drugs according to the invention in humans, their preventive or properly speaking curative action is displayed principally against certain diseases of the liver, such as hepatic steatosis (fatty liver), in particular nonalcoholic hepatic steatosis, and hepatic encephalopathy, against some endocrine and metabolic diseases such as hyperinsulinemia, insulin resistance and obesity and also against infantile pathologic conditions such as autism, Attention Deficit Disorder (ADD) and Attention Deficit/Hyperactive Disorder (ADHD).

In the case of animals, the veterinary products find useful applications in the treatment of hepatic pathologies and of endocrine and metabolic diseases.

For conciseness, in the rest of the present description reference will be made exclusively to the prevention/treatment of hepatic steatosis (fatty liver) and nonalcoholic hepatic steatosis, also in view of the particular preventive and curative efficacy of the edible compositions and drugs of the present invention with respect to these pathologies.

Hepatic steatosis (or fatty liver) is defined as the excessive accumulation of lipids in the hepatocytes, with "excessive accumulation" meaning lipid accumulation exceeding the normal 5% of the weight of the liver. In macrovesicular hepatic steatosis, large droplets of triglycerides swell the hepatocytes, displacing their nucleus towards the periphery of the cells, as occurs in adipocytes. In microvesicular hepatic steatosis, small droplets of triglycerides accumulate in the hepatocytes, leaving the nuclei in a central position, and the hepatocytes then assume a foamy appearance.

Hepatic steatosis, which commonly causes limited increases in serum aminotransferases (less than 4 times the upper limit of the norm), is reliably identified by imaging techniques such as ultrasonography and computerized tomography.

Nonalcoholic hepatic steatosis (often called NonAlcoholic SteatoHepatitis, NASH) is a clinical syndrome of steatosis accompanied by hepatic inflammation.

This is diagnosed by hepatic biopsy after other causes of liver diseases (for example infections by the hepatitis B virus and hepatitis C virus) have been excluded and after abuse of alcohol (>20 g/day) has been excluded with certainty. Once such abuse has been excluded, the following possible etiologic factors should be considered:

| | |
|---|---|
| Dietary abnormalities | obesity |
| | total parenteral feeding |
| | rapid loss of body weight |
| Drugs | estrogens |
| | corticosteroids |
| | amiodarone |
| Metabolic diseases | abetalipoproteinemia |
| | hypobetalipoproteinemia |
| | Wilson's disease |
| | Weber-Cristian disease |
| | lipodystrophy of the limbs |
| Surgical alterations of the gastrointestinal system | jejunoileal bypass |
| | extensive resection of the small intestine |
| | gastroplasty. |

No specific cause of nonalcoholic hepatic steatosis is known. In the past, the typical patient affected by this pathology was described as a female subject, obese, with an excess of sugar in the blood that might be caused by diabetes. Furthermore, the patient might present an excess of blood triglycerides and suffer from coronary disease, thyroid disorders or hypertension. It has recently been reported that patients affected by nonalcoholic hepatic steatosis do not always correspond to this picture. One study was of both male and female subjects who were not overweight, were not diabetic and did not have an excess of blood triglycerides. Another group of patients who were diagnosed as having nonalcoholic hepatic steatosis comprised children between the ages of 9 and 16 years. Most of them were overweight but only two out of thirty suffered from diabetes.

There are no blood tests that make it possible to diagnose steatosis and nonalcoholic hepatic steatosis with certainty.

Increases in aminotransferases (aspartate transaminase AST and alanine transaminase ALT), which might also not occur, are the only biochemical indicators, however they are common to both pathologies. Normal biochemical values have been found in pathologically obese individuals, whose hepatic biopsies indicated progressive liver disease.

However, the AST/ALT ratio can be useful for distinguishing nonalcoholic hepatic steatosis from alcoholic hepatic steatosis, a pathology in which profound anatomopathologic changes in the liver can be caused by abuse of alcohol (ethanol). In alcoholic steatosis the AST/ALT ratio is typically greater than 2 whereas in nonalcoholic steatosis the levels of ALT are higher than those of AST.

At present there is no known specific treatment for nonalcoholic hepatic steatosis that meets with general approval. Obviously, patients who are obese, diabetic and have elevated values of blood triglycerides are advised to lose weight and keep their diabetes under control by adopting a hypocaloric, low-fat diet, as well as taking insulin or medicines for lowering the blood sugar level. For an exhaustive review of the pathogenesis, clinical aspects, diagnosis and treatment of NASH, see Sheth S. G. et al., Nonalcoholic steatohepatitis, Ann. Intern. Med. 1997, 127–137, an article that is incorporated for reference in the present description.

The lack of an effective and generally accepted treatment constitutes a risk factor, because, whereas non-inflammatory steatosis is a benign condition, from 10 to 50% of patients affected by nonalcoholic hepatic steatosis develop a progressive fibrosis which can in its turn degenerate into cirrhosis, the eleventh most common cause of death in the West, for example in the United States.

It is therefore felt necessary to have at our disposal an effective preventive/curative means for the treatment of hepatic steatosis and, in particular, nonalcoholic hepatic steatosis, and it is therefore the purpose of the present invention to make such a means available.

According to the invention, the said means consists of a new, biologically pure strain of *Streptococcus thermophilus* ssp. *salivarius* (CD8), deposited on 4 Dec. 2001 at the DSMZ—Deutsche Sammlung von Mikroorganismen und Zellkulturen GmbH, Braunschweig, Germany, with accession No. DSM 14667 and its descendants and mutants.

The invention further relates to compositions that contain the aforesaid strain of *Streptococcus* as active principle, which can assume the form and perform the activity of edible products or dietary supplements, or of a medicine proper, or veterinary products, as a function of the supportive or preventive action, or therapeutic action proper, that the compositions are intended to perform, depending on the particular subjects for whom it is intended.

The invention also includes the use of the aforesaid strain for preparing compositions suitable for the prevention/treatment of the hepatic, endocrine and metabolic diseases previously enumerated or of autism and ADD or ADHD, and a preventive/therapeutic method based on the administration, preferably by the oral route, of the aforesaid compositions.

Although an interpretation of the mechanisms by which the new strain of *Streptococcus* CD8 exerts its preventive/curative action is not necessary for the understanding and practical application of the present invention, it can be postulated that the progress of benign and nonalcoholic hepatic steatosis (NASH) is inhibited by the changes induced by the *Streptococcus* in the signals of the inflammatory cytokines, by improvement of the function of the epithelial barrier and by inhibition of translocation of other bacteria from the intestine. These mechanisms are not mutually exclusive and it is probable that the new strain of *Streptococcus* is endowed with multiple activities.

Compositions based on lactic acid bacteria that have a protective action on the gut are known, but compositions that would reduce or antagonize benign hepatic steatosis or nonalcoholic hepatic steatosis were not known.

The compositions according to the invention that contain a preventatively or therapeutically effective quantity of *Streptococcus thermophilus* ssp. *salivarius* (CD8) or of its descendants or mutants can be formulated as edible compositions or dietary supplements, as drugs or veterinary products, in which the aforesaid *Streptococcus* is the only active ingredient or is mixed with one or more other active ingredients and/or one or more pharmacologically acceptable excipients. Selection of the excipients and of the most appropriate methods of formulation in view of the particular purpose of the compositions is within the scope of ordinary persons skilled in food or pharmaceutical technology.

A particularly preferred composition contains a strain of the aforesaid *Streptococcus* CD8 and a strain of *Lactobacillus brevis* CD2. The latter is deposited at the DSMZ—Deutsche Sammlung von Mikroorganismen und Zellkulturen GmbH, Braunschweig, Germany, with accession No. DSM 11988.

The preceding composition can further contain a strain selected from the group comprising *Bifidobacterium infantis*, *Bifidobacterium breve*, *Bifidobacterium longum*, *Bifidobacterium bifidum*, *Lactobacillus plantarum*, *Lactobacillus casei*, *Lactobacillus bulgaricus*, *Lactobacillus acidophilus* or their mixtures.

The preceding compositions can further contain at least one of the following ingredients: vitamin E, choline, ursodeoxycholic acid, clofibrate, tiglitazone, gemfibrozil, betaine, N-acetylcysteine, rosiglitazone, basic amino acids, L-carnitine or a lower alkanyl L-carnitine or their pharmacologically acceptable salts.

Preferred lower alkanyl L-carnitines are acetyl, propionyl and isovaleryl L-carnitine. Pharmacologically acceptable salts of L-carnitine are the fumarate and the tartrate, whereas pharmacologically acceptable salts of the alkanyl L-carnitines are the chloride, the fumarate and the galactarate.

Compositions suitable for oral administration can be in the form of a single dose, for example tablets, capsules and packets, or in the form of powders and granules or, alternatively, in the form of suspensions or emulsions.

The tablets and the capsules can contain binders, lubricants, stabilizers, coloring matter, separating agents and the like. The tablets can be coated using well-known techniques.

The liquid compositions can be in the form of aqueous or oily suspensions, for example in edible oils, or can be prepared as required by the user, by dissolving or suspending the preparation in the form of powder or granules in water or other suitable solvents.

These liquid compositions can contain suspending agents, emulsifiers, preservatives and the like.

It is preferable for the various dosage forms described above to contain a quantity of *Streptococcus thermophilus* ssp. *salivarius* (CD8) sufficient so that the user, complying with a dosing regimen that is easy to follow, can take from 50 to 3 600 billion bacteria of the strain per day.

We shall now describe clinical studies in which patients with nonalcoholic hepatic steatosis were enlisted. The diagnosis of nonalcoholic hepatic steatosis must include exclusion of infection by the hepatitis C virus (i.e. of the antibody to the hepatitis C virus) and of infection by the hepatitis B virus (surface antigens of hepatitis B). The levels of ceruloplasmin and of α-1-antitrypsin are usually normal in patients with nonalcoholic hepatic steatosis. The serologic autoimmune parameters (antimitochondrial antibody, antinucleating antibody, anti-smooth muscle antibody and anti-liver/kidney microsomal antibody) are negative in patients affected by nonalcoholic hepatic steatosis, except in some patients who have a low titer of antinuclear antibody positivity (varying from 1:40 to 1:320).

Clinical Study 1

Twenty-four patients (ten male and fourteen female, average age 49±12 years) who had been diagnosed as having the condition of nonalcoholic hepatic steatosis on the basis of compatible serum tests demonstrating elevated values of alanine transaminase were enlisted for the study. All of the patients received, per day, 1800 billion bacteria of *Streptococcus thermophilus* ssp. *salivarius* (CD8) freeze-dried in the form of granules.

The biochemical serum parameters, measurement of body weight and the lipid profile were determined at the time of admission to the study and after 3 months of therapy. Twelve patients out of twenty-four (50%) were obese (>20% above the ideal body weight). Eleven patients used oral hypoglycemics and/or insulin or had fasting glucose values >160 mg/dl.

The values for average serum alkaline phosphatase (Alk. phosph.), alanine transaminase (ALT) and gamma-glutamyl transpeptidase (GGT) after 3 months of therapy had decreased significantly relative to the base values on admission (T <0.01), as shown in the following table, in which the values are expressed in IU/l.

|  | Normal values | Before treatment | After treatment |
|---|---|---|---|
| Alk. phosph. | 98–275 | 322 ± 83 | 214 ± 44 |
| ALT | 0–42 | 96 ± 21 | 38 ± 12 |
| GGT | 11–50 | 72 ± 23 | 41 ± 16 |

No significant changes were detected in triglycerides, cholesterol and body weight. The data given in the table show that treatment of nonalcoholic hepatic steatosis with *Streptococcus thermophilus* ssp. *salivarius* (CD8) leads to a significant improvement in the levels of alkaline phosphatase, ALT and GGT, which are serum enzymes indicative of hepatic functions such as cytolysis and cholestasis.

Clinical Study 2

Five patients were enlisted in the study: two male and three female, who had increased levels of aspartate transaminase (AST) and alanine transaminase (ALT) and on whom a hepatic biopsy had been carried out which revealed a condition of nonalcoholic hepatic steatosis that had developed within the six months preceding their enlistment in the study. These patients did not show signs of other chronic liver diseases and were not taking drugs for lowering triglycerides. For four months, each patient received 1800 billion bacteria per day of the following species:
*Streptococcus thermophilus* ssp. *salivarius* (CD8)
*Lactobacillus brevis* (CD2)
*Bifidobacterium infantis*
*Lactobacillus plantarum*
*Lactobacillus casei*
*Lactobacillus bulgaricus*
*Lactobacillus acidophilus*
Each gram of the composition contained:
*Streptococcus thermophilus* ssp. *salivarius* (CD8)—150 billion
*Lactobacillus brevis* (CD2)—10 billion
*Bifidobacterium infantis*—100 billion
*Lactobacillus plantarum*—10 billion
*Lactobacillus casei*—10 billion
*Lactobacillus bulgaricus*—30 billion
*Lactobacillus acidophilus*—30 billion
The serum levels of AST and ALT were measured on entering the study and at the sixteenth week.

The study was completed by all five patients without any negative reactions being displayed.

The results of the study are presented in the following table, in which the results are expressed in IU/I.

|  | Normal values | Before treatment | After treatment |
|---|---|---|---|
| AST | 0–40 | 109 ± 23 | 45 ± 19 |
| ALT | 0–42 | 114 ± 29 | 48 ± 18 |

Nor in this study were changes found in the lipid profile (cholesterolemia, triglycerides) confirming the specificity of action of the preceding composition containing *Streptococcus thermophilus* ssp. *salivarius* (CD8) in combination with other lactic acid bacteria. The composition was formulated so as to display, in combination, the properties of *Streptococcus thermophilus* ssp. *salivarius* (CD8) with the anti-inflammatory properties of the other lactic acid bacteria (for example of *Lactobacillus brevis* CD2, see international patent application WO 99/42568).

The invention claimed is:

1. A biologically pure strain of *Streptococcus thermophilus* ssp. *salivarius* (CD8) deposited on 4 Dec. 2001 at the DSMZ—Deutsche Sammlung von Mikroorganismen und Zellkulturen GmbH, Braunschweig, Germany, with accession No. DSM 14667.

2. A composition containing a strain of *Streptococcus thermophilus* ssp. *salivarius* of claim 1.

3. A composition containing a biologically pure strain of *Streptococcus thermophilus* ssp. *salivarius* (CD8) deposited on 4 Dec. 2001 at the DSMZ—Deutsche Sammlung von Mikroorganismen und Zellkulturen GmbH, Braunschweig, Germany, with accession No. DSM 14667 together with a binder, stabilizer, colorant, separating agent, edible oil, water suspending agent, emulsifier or preservative.

4. A unit dosage form containing 50 to 3,600 billion bacteria of the biologically pure strain of *Streptococcus thermophilus* ssp. *salivarius* (CD8) deposited on 4 Dec. 2001 at the DSMZ—Deutsche Sammlung von Mikroorganismen und Zellkulturen GmbH, Braunschweig, Germany, with accession No. DSM 14667.

* * * * *